US006445949B1

(12) United States Patent
Kroll

(10) Patent No.: US 6,445,949 B1
(45) Date of Patent: Sep. 3, 2002

(54) IMPLANTABLE CARDIOVERSION DEVICE WITH A SELF-ADJUSTING THRESHOLD FOR THERAPY SELECTION

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/478,300

(22) Filed: Jan. 5, 2000

(51) Int. Cl.[7] .................................................. A61N 1/37
(52) U.S. Cl. .............................. 607/4; 607/14; 600/518
(58) Field of Search ........................... 607/4, 5, 14, 27, 607/30; 600/515, 518, 519

(56) References Cited

U.S. PATENT DOCUMENTS

| | | | | |
|---|---|---|---|---|
| 4,712,555 A | | 12/1987 | Thornander et al. | 128/419 |
| 4,788,980 A | | 12/1988 | Mann et al. | 128/419 |
| 4,809,697 A | | 3/1989 | Causey, III et al. | 128/419 |
| 4,940,052 A | | 7/1990 | Mann et al. | 128/419 |
| 4,944,298 A | | 7/1990 | Sholder | 128/419 |
| 4,944,299 A | | 7/1990 | Silvian | 128/419 |
| 5,002,052 A | * | 3/1991 | Haluska | 128/419 |
| 5,342,402 A | * | 8/1994 | Olson et al. | 607/5 |
| 5,403,352 A | * | 4/1995 | Rossing | 607/4 |
| 5,836,971 A | * | 11/1998 | Starkweather | 607/4 |
| 5,851,220 A | * | 12/1998 | Murphy | 607/5 |
| 5,882,352 A | * | 3/1999 | Duncan et al. | 607/4 |
| 6,230,055 B1 | * | 5/2001 | Sun et al. | 607/5 |

OTHER PUBLICATIONS

Schaumann, Anselm, MD, et al "Empirical Versus Tested Antitachycardia Pacing in Implantble Cardioverter Defibrillators, A Prospective Study Including 200 Patients," American Heart Association; pp. 67–74; (1998).

Bach, Stan M. et al "Implantable Cardiverter Defibrillator Therapy," Kluwer Academic Publishers; pp. 305–307 (1996).

* cited by examiner

Primary Examiner—Kennedy Schaetzle

(57) ABSTRACT

In an implantable cardioversion device, the condition of the patient's heart is determined from an intrinsic ventricular parameter, such as the ventricular rate, and therapy is provided with a shock or pulse generator, including, for instance, antitachycardia pacing therapy or defibrillation shocks. Initially, the conditions, i.e., ventricular tachycardia or fibrillation/flutter, are determined using predetermined values for a set of thresholds defining the various conditions. Thereafter, the thresholds are changed by increasing or decreasing the therapy thresholds from the predetermined values based on the success rate of the corresponding therapy.

39 Claims, 7 Drawing Sheets

| INTERVAL THRESHOLDS | CARDIAC CONDITION |
|---|---|
| | VENTRICULAR FIBRILLATION (VF) |
| VFI | |
| | FAST VT |
| VT2I | VENTRICULAR TACHYCARDIA (VT) |
| | SLOW VT |
| VT1I | |
| | NORMAL SINUS RHYTHM (NSR) |
| BRI | |
| | BRADYCARDIA |

FREQUENCY / DURATION

FIG. 3

| VENTRICULAR RATE BPM | INTERVAL MS | POSSIBLE DIAGNOSIS | | | |
|---|---|---|---|---|---|
| | | VF | AF | VT | NSR |
| 500 | 120 | X | | | |
| | 140 | X | | | |
| | 160 | X | | | |
| | 180 | X | | | |
| 300 | 200 | X | | | |
| | 220 | X | | | |
| | 240 | X | | | |
| | 260 | X | X | | |
| | 280 | X | X | X | |
| 200 | 300 | X | X | X | |
| | 320 | X | X | X | |
| | 340 | X | X | X | |
| | 360 | X | X | X | |
| | 380 | | X | X | |
| 150 | 400 | | X | X | |
| | 420 | | X | X | |
| | 440 | | X | X | |
| | 460 | | X | X | X |
| | 480 | | X | X | X |
| | 500 | | X | X | X |
| 120 | 520 | | | | X |
| | 540 | | | | X |
| | 560 | | | | X |
| | 580 | | | | X |
| 100 | 600 | | | | X |
| | 620 | | | | X |
| | 640 | | | | X |

FIG. 4

IMPLANTABLE CARDIOVERSION DEVICE WITH A SELF-ADJUSTING THRESHOLD FOR THERAPY SELECTION

FIELD OF THE INVENTION

This invention pertains to implantable cardioversion devices (ICDs) which sense a dangerous cardiac arrhythmia and, in response, provide therapy to the patient's heart to revert it to a normal sinus rhythm. More particularly, the invention pertains to implantable medical devices and methods, such as an ICD including a sensor for sensing intrinsic cardiac activity and a cardioverter/defibrillator adapted to provide different types of antitachycardia therapy dependent upon the condition of the heart as indicated by the sensor. The ICD is further provided with an automated threshold adjustment means for setting the threshold(s) delimiting the therapies.

BACKGROUND OF THE INVENTION

As used herein, the term "abnormal arrhythmia" refers to any abnormal heart rhythm that may be dangerous to the patient and specifically includes fibrillation, tachycardias, supraventricular tachycardias (SVT), ventricular tachycardias (VT), ventricular fibrillation and flutter (VF), and bradycardia. As further used herein, the term "therapy" refers to any means used by the ICD to restore normal heart rhythm such as defibrillation, cardioversion, antitachycardia pacing (ATP), antibradycardia therapy and drug infusion. The disclosed invention has application to ICDs which treat tachyarrhythmias (abnormally high heart rates).

It has been common practice to monitor the heart rate, or more commonly the ventricular rate, of a patient and classify the cardiac condition of the patient based on this heart rate. (Other criteria, in addition to the ventricular rate, may also be used for this classification, but these criteria are omitted for the sake of clarity). For example, tachyarrhythmia may be defined as any rate in a range above a designated threshold VT1. This range is then divided into ventricular tachycardia and ventricular fibrillation (and flutter) zones. The ventricular tachycardia zone may be further divided into slow ventricular tachycardia and fast ventricular tachycardia zones.

Once it is determined that a patient suffers from one of these cardiac conditions, the ICD is programmed to provide a corresponding therapy. Typically, ventricular tachycardia is treated with a therapy consisting of low-energy pacing pulses designed to capture the ventricle. This therapy is referred to as AntiTachycardia Pacing therapy (ATP). Ventricular fibrillation, on the other hand, is treated more aggressively with high energy shocks. The ICD is programmed with parameters for various types of therapies and the rates defining the therapy zones corresponding to the respective therapies.

Over the years, the number of programmable parameters has been increasing steadily. A modern ICD has up to 200 or more programmable parameters. A major challenge for both the ICD manufacturer and the clinician is to select proper values for these parameters. While the manufacturer may provide nominal or default values for the parameters, these nominal values may not be proper for all patients and it is up to the clinician to change them using statistical information and his personal experience. However, changing and adapting the parameters have proven to be difficult and it has been found that most clinicians leave the majority of the parameters at their nominal values.

Some of the parameters, however, including the thresholds defining the antitachycardia therapies described above, should be changed periodically to conform to the changing condition of the patient.

It is, hence, desirable to provide an ICD capable of selecting or adjusting some of its parameters automatically so that the clinician does not have to set them on implantation or adjust them each time the condition of the heart changes. More importantly, it would be advantageous to provide an ICD which can adjust some of its parameters adaptively, quickly and efficiently setting them at their optimal levels, and resetting or re-adjusting them automatically as the condition of the patient changes.

The present invention addresses the problem of automatically and dynamically adjusting the thresholds which define the various tachyarrhythmia therapy zones.

SUMMARY OF THE INVENTION

In its broadest sense, the present invention pertains to an ICD which includes a timing and control circuit adapted to classify the condition of a patient as being one of certain preselected types of cardiac conditions based essentially, but not necessarily exclusively, upon the heart rate. The ICD further includes a circuit for selecting and setting thresholds which define the therapy zones corresponding to cardiac conditions. These thresholds are adaptively changed to conform to the individual characteristics and requirements of the patient. In this manner, the ICD can be programmed with initial thresholds, selected either by the manufacturer or the clinician, which are based on statistical information from other patients, etc. These thresholds are then automatically adjusted by the ICD over time. Thus, the clinician does not need to change the default settings or reprogram the ICD during a subsequent visit if the condition of the patient changes.

More particularly, the present invention contemplates an ICD comprising a sense amplifier that generates a sense signal indicative of intrinsic events in the ventricle; a control and timing circuit which generates control signals responsive to the sense signal to define a tachyarrhythmia therapy; a pulse generator that receives the control signals and generates corresponding output signals delivered to the patient's heart; and a threshold setting circuit for setting the thresholds which define the various zones characteristic of specific cardiac conditions associated with tachyarrhythmia. Importantly, a success rate circuit is also provided which monitors whether a particular therapy, defined by the control signals, is successful. This information is used to determine whether a particular threshold should be changed and, if so, whether the particular threshold should be raised or lowered. Preferably, the ICD is also provided with a memory for storing various programming and operational parameters, as well as a set of rules for setting each threshold.

BRIEF DESCRIPTION OF THE DRAWINGS

The above and other aspects, features and advantages of the present invention will be more apparent from the following more particular description thereof, presented in conjunction with the following drawings wherein:

FIG. 3 shows graphically the zones for various cardiac rhythms used by the ICD;

FIG. 4 shows actual cardiac conditions with overlapping ventricular rates or intervals.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable medical devices, including an ICD. To better understand the invention, it will first be helpful to have an understanding of the basic functions performed by an exemplary implantable medical device with which the invention is used, e.g., an ICD. To that end, reference is first made to FIG. 1, where there is shown a simplified functional block diagram of an ICD 20. It should also be noted that, in some instances, the functions of an ICD and a pacemaker may be combined within the same medical device. However, for purposes of the explanations that follow, only an ICD is described herein.

Figure 1:
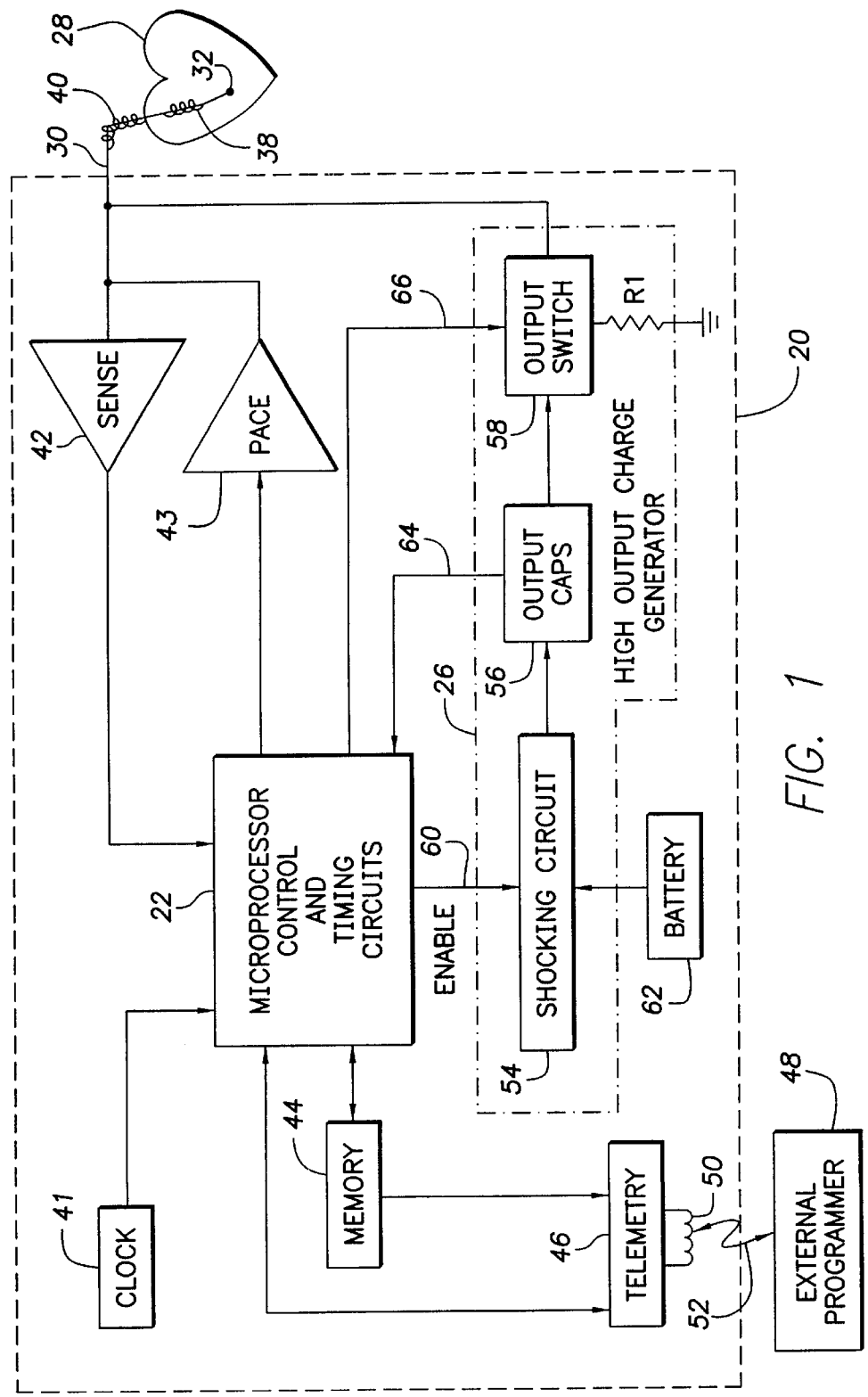
FIG. 1 shows a simplified functional block diagram of an ICD, which represents one type of implantable medical device with which the present invention may be used.

It is the primary function of an ICD to sense an arrhythmia and attempt to terminate it automatically by applying an appropriate electrical shock to the heart. To this end, ICD 20, as shown in the functional block diagram of FIG. 1, includes a microprocessor-based control and timing circuit 22 (hereafter "control/timing" circuit 22) that controls an output charge generator 26. The output charge generator 26 receives power from battery 62 and generates electrical stimulation pulses of moderate or high energy (cardioversion or defibrillation pulses), e.g., electrical pulses having energies of from 1 to 10 joules (moderate) or 11 to 40 joules (high), as controlled by the control/timing circuit 22. Such moderate or high energy pulses are applied to the patient's heart 28 through at least one lead 30 which is coupled to suitable implanted electrodes 38 and 40, positioned in the heart 28. While only one lead and two electrodes are shown in FIG. 1, it is to be understood that additional defibrillation leads and electrodes may be used as desired or needed in order to efficiently and effectively apply the shock treatment generated by the output charge generator 26 to the heart 28.

Alternatively, for less severe tachyarrhythmias such as ventricular tachycardia, pacing pulses may be applied by the output charge generator 26 in response to commands from control/timing circuit 22.

The ICD 20 also includes a sense amplifier 42 that is coupled to sensing lead 30 and electrode 32. Sense amplifier 42 senses the activity of the heart 28 by detecting certain electrical signals sensed through the electrode 32. As is known in the art, R-waves occur upon the depolarization, and hence contraction, of ventricular tissue; and P-waves occur upon the depolarization, and hence contraction, of atrial tissue. Thus, by sensing R-waves and/or P-waves through the sense amplifier 42, and providing such sensed signals to the control/timing circuit 22, the control/timing circuit 22 is able to make a determination as to the rate and regularity of the patient's heart beat. Such information, in turn, allows the control/timing circuit 22 to determine whether the heart 28 is experiencing an arrhythmia.

The control/timing circuit 22 further has a memory circuit 44 coupled thereto wherein the operating parameters used by the control/timing circuit 22 are stored. Such operating parameters define, for example, the amplitude of each shock energy pulse to be delivered to heart 28 within each tier of therapy, and its duration. The memory 44 may take many forms, and may be subdivided into as many different memory blocks or sections (addresses) as needed to store desired data and control information. A feature of the present invention, in some embodiments thereof, is the ability to sense and store a relatively large amount of data as a data record, which data record may then be used to guide the operation of the device, i.e., the present operating mode of the device may be dependent, at least in part, on past performance data.

Advantageously, the operating parameters of the ICD 20 may be non-invasively programmed into the memory 44 through a telemetry circuit 46, which is in telecommunications contact with an external programmer 48 by way of a suitable coupling coil 50. The coupling coil 50 may serve as an antenna for establishing a radio frequency (RF) communication link 52 with the external programmer 48 or the coil 50 may serve as a means for inductively coupling data between the telemetry circuit 46 and the external programmer 48, as is known in the art. See, e.g., U.S. Pat. No. 4,809,697 (Causey, III et al.) and U.S. Pat. No. 4,944,299 (Silvian), incorporated herein by reference. Further, the telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, or similar processing circuit, which is capable of processing or monitoring input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that carries out the functions described herein. The use, design, and operation of microprocessor-based control circuits to perform timing and data analysis functions is known in the art. The telemetry or communications circuit 46 may be of conventional design, such as is described in U.S. Pat. No. 4,944,299, or as is otherwise known in the art.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described and U.S. Pat. No. 4,788,980, wherein the various timing intervals used within the pacemaker and their inter-relationships are more thoroughly described. The '052, '555, '298 and '980 patents are incorporated herein by reference.

As previously mentioned, an important feature of the present invention is that it is able to adapt itself automatically to the individual characteristics of the patient thereby eliminating the lengthy, uncomfortable testing period required to determine and set the various thresholds that have been required with standard ICD implantations until now. The invention is best understood by describing its normal mode of operation.

Figure 2:
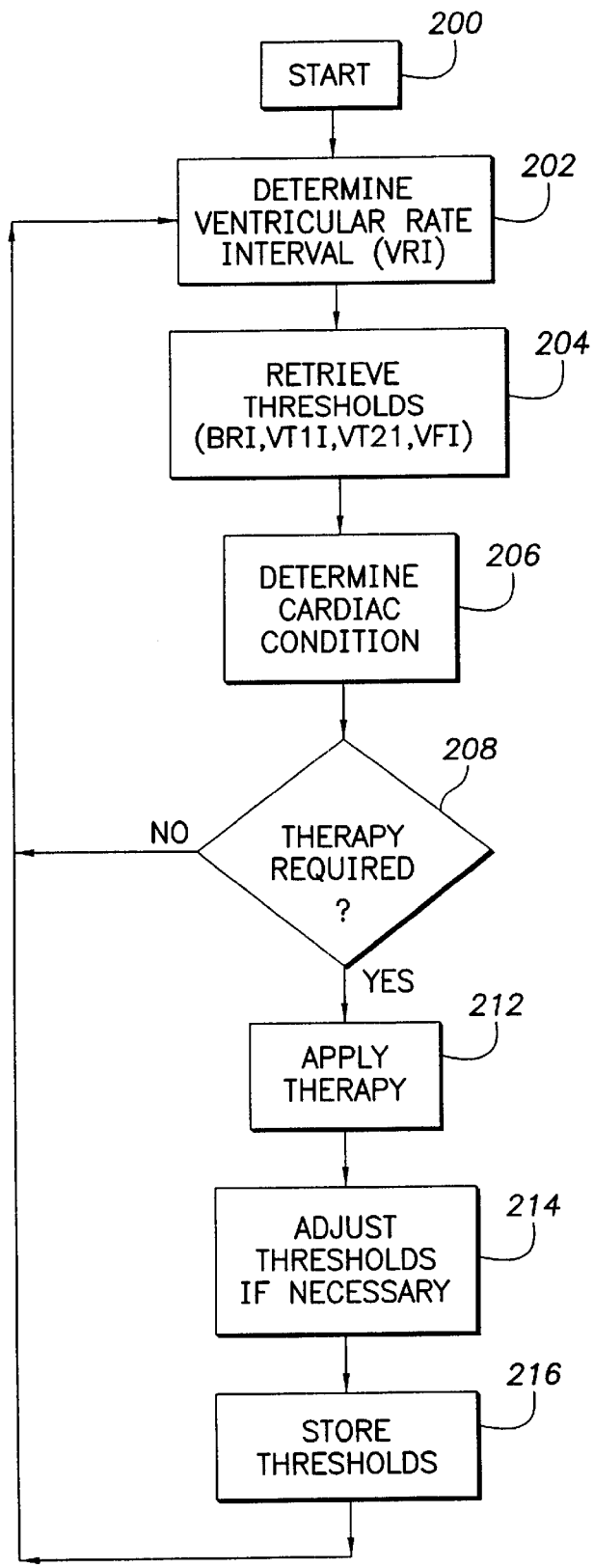
FIG. 2 shows a flow chart for the operation of the ICD in accordance with this invention.

Referring now to FIG. 2, after implantation, operation of the ICD 20 begins at START step 200. In step 202, the ICD determines the ventricular rate interval (VRI) corresponding to the current ventricular rate (VR) of the intrinsic ventricular beat of the heart using, for example, information received from sense amplifier 42. In step 204, the control/timing circuit 22 retrieves from memory 44 the current interval thresholds which define the various cardiac zones. Initially, these interval thresholds are either preprogrammed by the manufacturer or are set by the clinician after implantation, using the patient's age, health, prior cardiac history, and present condition as criteria.

FIG. 3 shows a typical cardiac condition classified into zones by heart rate intervals stored in memory 44. The heart rate increases as the time interval between heart beats decreases. Accordingly, while FIG. 3 shows zones which increase upwards in frequency ranges, the designated interval thresholds, i.e., BRI, VT1I, VT2I,and VFI decrease in time duration as the corresponding frequency ranges increase. In a preferred implementation of the present invention, the thresholds used correspond to the intervals between heart beats since hardware for measuring intervals, i.e., time durations, is generally easier to implement than hardware that measures rates, i.e., frequencies. However, implementations that determine heart rates and therefore use rate thresholds are considered to be alternative implementations of the present invention.

A ventricular rate interval (VRI) greater than the bradycardia interval threshold BRI (i.e., below a bradycardia frequency threshold) is classified as bradycardia. Between interval thresholds BRI and VT1I (the interval threshold for a slow ventricular tachycardia), the cardiac rate is at a normal sinus rhythm. Between interval thresholds VT1I and VFI (the interval threshold for indicating ventricular fibrillation), the heart condition is classified as ventricular tachycardia (VT). Frequently this condition is partitioned into two zones, slow VT and fast VT, by an interval threshold VT2I, with a different antitachyarrhythmic pacing regimen or other therapy being applied for each zone. The two therapies are referred to herein as ATP1 and ATP2, respectively. When the ventricular rate interval (VRI) is less than the VFI interval threshold (i.e., when the heart rate exceeds a ventricular fibrillation rate), the cardiac condition is classified as ventricular fibrillation or flutter which is normally treated by shock therapy. The interval thresholds BRI, VT1I, VT2I and VFI are determined for each patient by the clinician, as described above, immediately following implantation or, alternatively, by initial use of standard default settings. It should be understood that the scheme in FIG. 3 may be used to classify patient cardiac conditions and to determine what therapy (if any) should be applied to the patient for each condition. Other criteria may refine this determination, which is beyond the scope of this application. A discussion of some of these criteria is found in "IMPLANTABLE CARDIOVERTER DEFIBRILLATOR THERAPY" edited by Mark W. Kroll, Ph.D. and Michael H. Lehmann, M.D., Kluwer Academic Publishers, 1996, pp. 305–307.

FIG. 4 shows a table indicating measured ranges for the ventricular rates and time intervals (which are the inverse of the ventricular rates) corresponding to various cardiac conditions. As can be seen from this figure, there is considerable overlap between ventricular rates corresponding to VF (ventricular fibrillation), AF (atrial fibrillation), VT (ventricular tachycardia) and NSR (normal sinus rhythm). Accordingly, ventricular rate by itself may not be sufficient for a prognosis if the interval thresholds of FIG. 3 are maintained at predetermined levels.

What is contemplated in the present invention is the dynamic adjustment of the interval thresholds (or conversely the corresponding frequency thresholds) by the ICD, which can be accomplished as follows. Initially, the values of the various interval thresholds (whether preset, or programmed by the clinician) are stored in memory 44. Referring again to FIG. 2, after the current ventricular rate interval (VRI) is determined in step 202, the initial interval thresholds are retrieved in step 204 from memory 44. In step 206, the cardiac condition of the patient is determined using the current value of the ventricular rate interval (VRI) and the condition classification scheme of FIG. 3. In step 208, a determination is made as to whether therapy is required. If no therapy is required, then a new value for the ventricular rate interval (VRI) is determined based on the next intrinsic cardiac event.

If the current ventricular rate interval (VRI) is outside the NSR (normal sinus rhythm) zone, then, in step 212, a therapy is selected that is appropriate to the applicable classification defined by the zones of FIG. 3. During or after the application of therapy, the interval thresholds are adjusted (if necessary) in step 214 (as discussed below) and the new interval thresholds are stored in step 216. Following the next ventricular rate interval (VRI) determination of step 202, these new thresholds are retrieved in step 204 and used for subsequent threshold interval determinations.

Exemplary initial values for the interval thresholds, as well as the upper and lower limits in milliseconds (ms) are set as follows (since the invention pertains to ICDs designed primarily for antitachycardia therapy, a discussion of the bradycardia interval threshold (BRI) is omitted herein):

| INTERVAL THRESHOLD | INITIAL OR DEFAULT | MINIMUM | MAXIMUM |
| --- | --- | --- | --- |
| VT1I | 400 ms | 300 ms | 500 ms |
| VT2I | 320 ms | Max{(VFI + 20), 260} ms | Max{(VTI1-20), 400} ms |
| VFI | 280 ms | 200 ms | 400 ms | wherein VFI refers to the ventricular fibrillation threshold interval, VT1I and VT2I refer to threshold intervals for determining the range of ventricular tachycardia and Max {A, B} refers to an operation for choosing the larger of A and B.

Initially, based on these limits (and perhaps other criteria as set forth above), the control/timing circuit 22 first determines the patient's cardiac condition. More specifically, the-control/timing circuit 22 determines the cardiac condition as being bradycardia, normal sinus rhythm, slow VT, fast VT or ventricular fibrillation. Therapy for the various arrhythmia conditions are known in the art, as discussed for example in the above-mentioned textbook "IMPLANTABLE CARDIOVERTER DEFIBRILLATOR THERAPY" and will not be discussed here in detail.

Figure 5A:
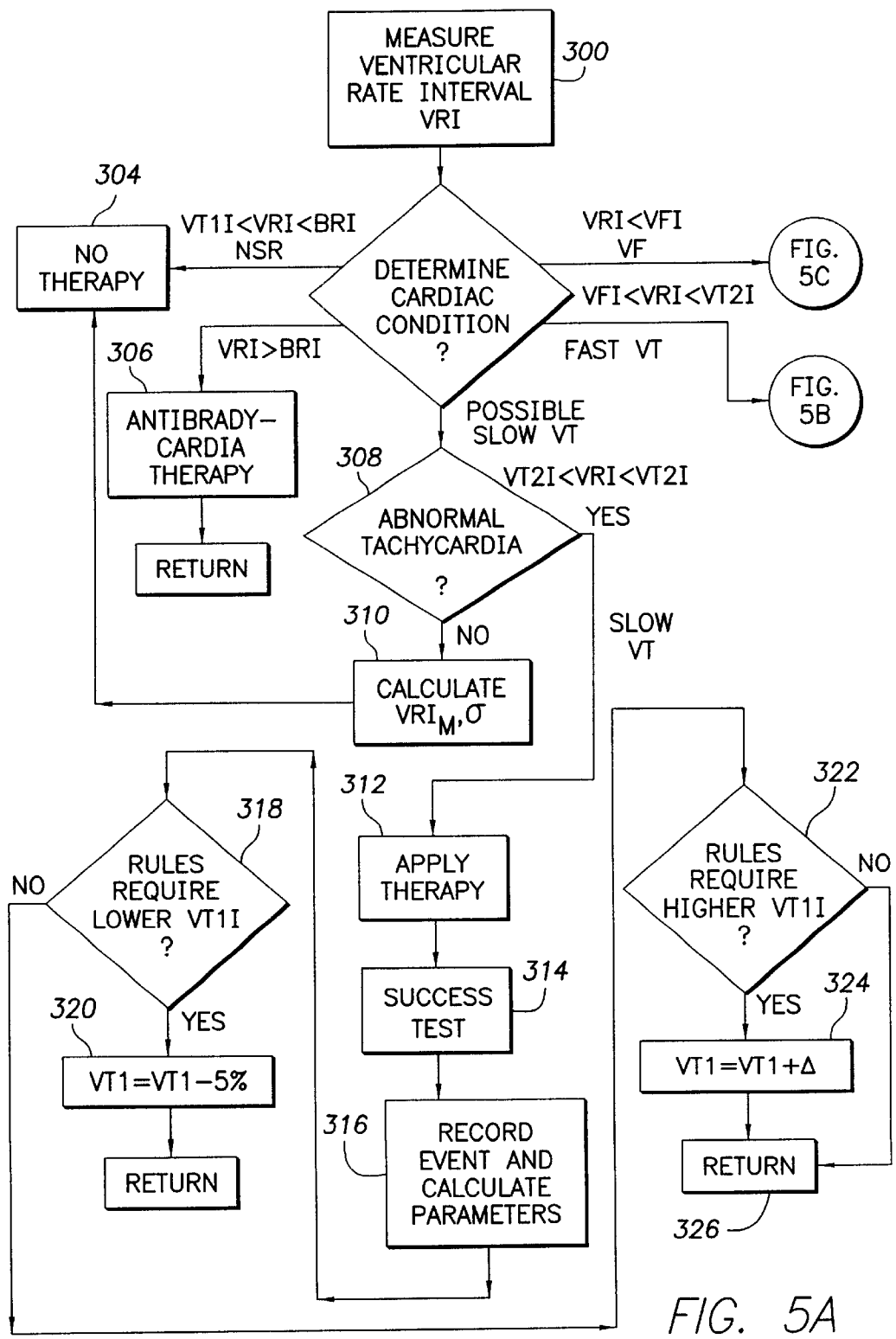
FIGS. 5A, B and C show a detailed flow chart of an exemplary method used by an ICD to dynamically adjust the thresholds defining the therapy zones.
Figure 5B:
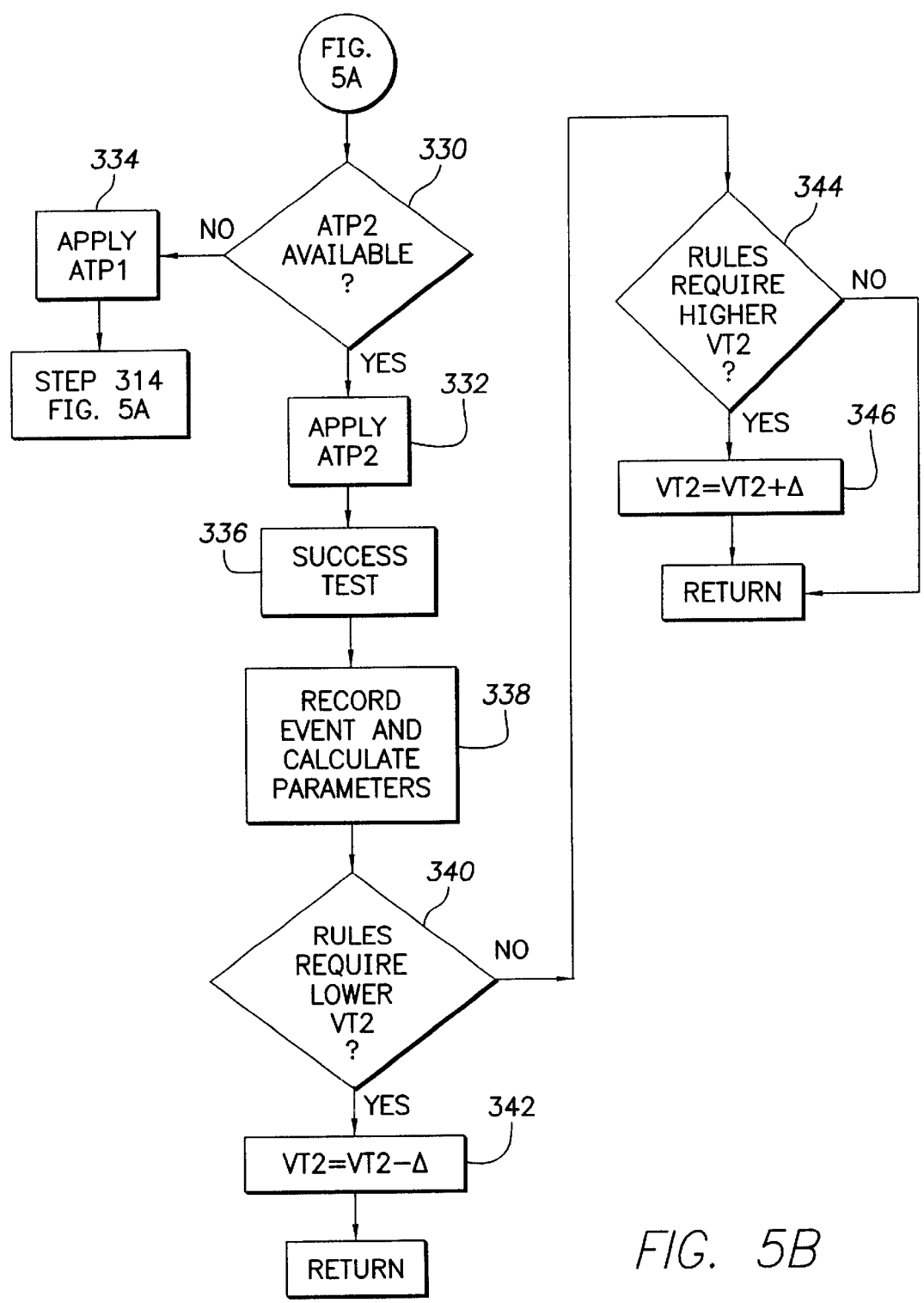
Figure 5C:
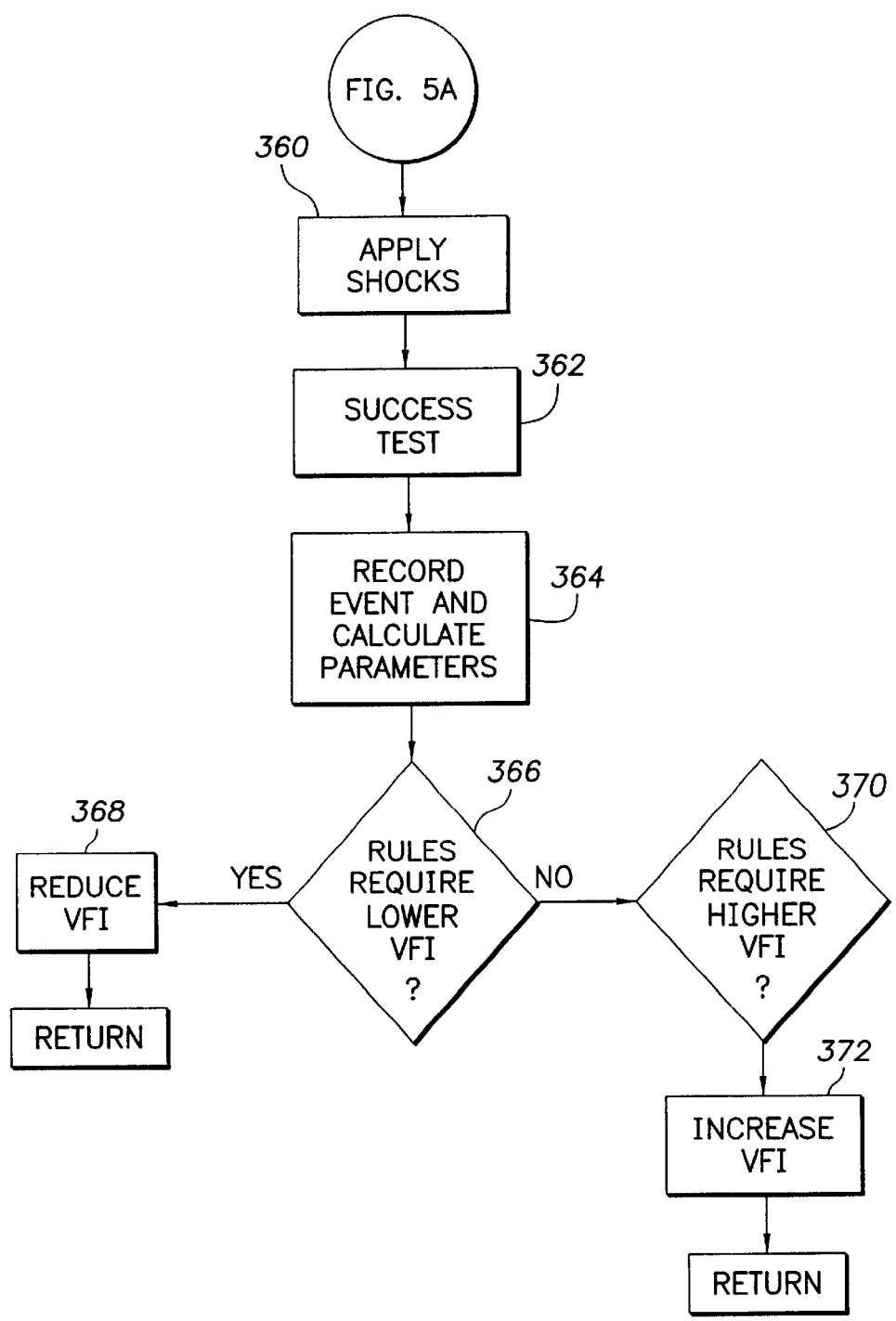

A more detailed description of an exemplary operation of control/timing circuit 22 is shown in FIGS. 5A–5C. Initially, in step 300, the ventricular rate interval (VRI) is measured. Then, in step 302, the current cardiac condition of the patient is determined, preferably using the ventricular rate interval as a criterion, as shown in FIG. 3. In an exemplary implementation, this determination is done by a software construct, e.g., a series of "IF-THEN-ELSE" statements, a "DO CASE" statement, or the like, which determines the next step to be processed by comparing the measured ventricular rate interval (VRI) to a series of interval thresholds, e.g., BRI, VT1I, VT2I, and VFI. As shown in FIG. 5A, if the ventricular rate interval (VRI) is between BRI and VT1I (VT1I<VRI<BRI), normal sinus rhythm is indicated at step 304 and no therapy is required. If the ventricular rate interval (VRI) is greater than BRI (VRI>BRI), then antibradycardia therapy is applied at step 306. If the ventricular rate interval VRI is between VT2I and VFI (VFI<VRI<VT2I), then a fast ventricular tachycardia (fast VT) condition is treated as described in FIG. 5B. If the ventricular rate interval VRI is less than VFI (VRI<VFI), then a ventricular fibrillation (VF) condition is treated as described in FIG. 5C. If a ventricular rate interval VRI is between VT1I and VT2I (VT2I<VRI<VT1I), then a slow ventricular tachycardia (slow VT) condition is determined. In step 308, a test is performed to determine or confirm that the detected condition is indeed an abnormal tachycardia, which may require therapy, and not an elevated normal sinus rhythm (ENSR, also referred to as a sinus tachycardia) due, for instance, to exercise. One test for distinguishing slow VT from an elevated normal sinus rhythm (ENSR) is to analyze the onset of the VT condition. For this purpose, in step 308, a baseline or average ventricular rate interval ($VRI_{av}$) is determined (for example, by averaging VRI for the last four beats), and the current value of VRI (i.e., the value which has been determined in step 302 to correspond to slow VT) is compared to this $VRI_{av}$. Slow VT is determined if the current VRI is less than $VRI_{av}$ by greater than a preselected ratio, such as 10%, indicating a fast onset that is characteristic of slow VT rather than ENSR. Conversely, the equivalent determination can be made by looking for an increase in the average ventricular rate. Other means of distinguishing ENSR from slow VT may be used as well.

If it has been determined that the patient's elevated heart rate is based upon an elevated normal sinus rhythm (ENSR), e.g., resulting from exercise, calculations are performed in step 310 to determine the statistics of the ventricular rate interval (VRI), including its mean value $VRI_M$ and its standard deviation $\sigma$. Once these parameters are obtained (preferably in milliseconds), they are used to determine whether the patient is relatively young and fit and to determine how the interval thresholds are adjusted in the following steps of the disclosed invention.

If step 308 does show a slow VT (i.e., an elevated normal sinus rhythm is not shown), then, in step 312, appropriate therapy is applied. In step 314, a test is performed to determine if the therapy applied in step 312 was successful. In step 316, the results of the test from step 314 are logged or recorded in memory 44. These results are tabulated over several abnormal VT events. In addition, several other parameters are also calculated and are used to determine whether the thresholds of FIG. 3 are appropriate. More particularly, step 318 utilizes a set of rules to determine, historically, whether the interval threshold VT1I needs to be adjusted, preferably by a predetermined amount, e.g., 5%. The following is an exemplary set of rules that may be applied in step 318 to determine if the interval threshold VT1I should be decreased and the corresponding frequency threshold increased:

A. $(VRI_M - 4\sigma) > VT1I$, and
B. over 90% of VT1I crossings ( i.e., excursions of VRI below VT1I) are not confirmed in step 308 as sudden onset.

Another set of rules for decreasing the threshold interval VT1I is:

C. $(\sigma/VRI_M) > 10\%$, and
D. 90% of the VT1I crossings are rejected by the fast onset criterion of step 308, and
E. The ATP1 success rate in the slowest 20% of VT events is less than 50%.

Alternatively, the following set of rules can be used in block 322 to determine if the interval threshold VT1I should be increased and the corresponding frequency threshold decreased:

F. $(VRI_M - 6\sigma) > VT1I$, and
G. The ATP1 success rate in the slowest 20% zone of VT events is over 80% (suggesting very little atrial fibrillation or normal sinus rhythm), and
H. 90% of the VT1I crossings are confirmed by the fast onset tests of steps 308 as being ventricular tachycardia (VT) and not an elevated normal sinus rhythm.

Referring again to FIG. 5A, the parameters required by these rules are calculated in step 310 and, in step 318, a determination is made using the rules set forth whether the threshold VT1I should be lowered. If yes, then, in step 320, the threshold setting circuit 80 decreases the threshold VT1I, preferably by a predetermined amount $\Delta$, e.g., 5%. In step 322, the rules above are used to determine if threshold VT1I should be increased. If yes, then, in step 324, the threshold VT1I is increased, preferably by a predetermined amount $\Delta$, e.g., 5%. If not, then VT1I remains the same (step 326).

FIG. 5B depicts the steps performed if fast VT is detected in step 302 of FIG. 5A. First, in step 330, a check is performed to determine if the ICD is configured or capable of performing fast VT therapy (ATP2) as a distinct therapy separate from the ATP1 therapy used for slow VT. The ICD may be set up so that the clinician is given the choice of either requesting a single or universal therapy, in case of all VTs, or requesting a different, i.e., bifurcated, therapy for slow and for fast VT.

If ATP2 therapy is available for fast VT, then, in step 332, ATP2 therapy is applied. If ATP2 therapy is not available, then, in step 334, ATP1 therapy is applied, and the process of FIG. 5A is continued with step 314.

In step 336, a test is performed to determine if the ATP2 therapy applied in step 332 was successful. The events are recorded in step 338 into memory 44. In step 338, a set of parameters is also calculated either after every VT episode or on a daily basis. More specifically, the number of times that the ATP1 therapy for slow VT has been successful in the last N (e.g., 10) slow VT events, and the number of times ATP2 therapy was successful for the last N fast VT events are determined. The parameters $VRI_M$ and $\sigma$ (defined above) are also determined.

In step 340, another set of rules determine whether the interval threshold VT2I needs to be changed. The following exemplary rules may be used to determine if the interval threshold VT2I should be decreased and the corresponding frequency threshold increased:

I. No unsuccessful therapy events occurred in the slow VT zone; and
J. $(VRI_m + \sigma)$ of the events with unsuccessful therapy in the fast VT zone is greater than VT2I.

If the rules in step 340 indicate that interval threshold VT2I is too high then, in step 342, the interval threshold VT2I is decreased, preferably by a predetermined amount $\Delta$, e.g., 5%. If not, in step 344, a test is performed to determine if the interval threshold VT2I needs to be increased and the corresponding frequency threshold decreased. The following is a set of exemplary rules which may be used in step 344 to this end:

K. The success rate of ATP2 therapy in the high VT zone is greater than the success rate of ATP1 therapy in the slow VT zone; and
L. The mean interval $+\sigma$ of successful ATP2 events in the high VT zone is greater than the mean of unsuccessful ATP1 events in the slow VT zone.

If the rules or conditions K–L are met, the interval threshold VT2I is increased in step 346, preferably by a predetermined amount Δ, e.g., 5%.

Referring now to FIG. 5C, if in step 302, a VF condition is identified, then, in step 360, therapy is applied appropriate to this condition. More particularly, for VF, one or more energy shocks are typically applied.

In step 362, the effectiveness and success of the therapy of step 360 is determined. In step 364, the results of the test of step 362 are recorded in memory 44. The parameters $VRI_M$ and σ are also calculated at this time.

In step 366, a set of rules determine whether the interval threshold VFI needs to be lowered and the corresponding frequency raised. A set of exemplary rules for decreasing VFI is as follows:

M. If $(VRI_M+2\sigma)$ of VFI events is less than VFI (over 10 shocks), then reduce VFI to $(VRI_M+2\sigma)$.

N. If a series of shocks is applied as part of therapy in step 360 and the whole series is unsuccessful, it is assumed that atrial fibrillation (AF) is present and VFI is reduced by 5%.

If the rules indicate that a decrease is necessary, then VFI is decreased in step 368.

If VFI is not required to be decreased then, in step 370, another set of rules is used to determine if VFI needs to be increased. A set of exemplary rules for increasing VFI are as follows:

O. If $(VRI_M+\sigma)$ of VFI events is greater than VFI over the last 10 shocks, increase VFI to $(VRI_M+\sigma)$.

P. If the ATP2 therapy for fast VT fails when the current VRI is within (i.e., higher than) a percentage (e.g., 10%) of VFI, increase VFI.

If these rules indicate an increase, then, in step 372, the threshold VFI is increased, as prescribed by the rules.

In this manner the interval thresholds VT1I, VT2I, VFI are automatically and adaptively adjusted by the ICD for the individual requirements and characteristics of each patient.

While the invention has been described by means of specific embodiments, it is understood that modification and variations could be made thereto by those skilled in the art without departing from the spirit and the scope of the invention. For example, while the patient condition zones have been defined using threshold intervals by measuring and comparing time durations, an equivalent function can be accomplished by using threshold frequencies and measuring and comparing frequencies. Additionally, while flow charts have been described, preferably for implementation by the microprocessor control/timing circuit in a software implementation, portions of the flow charts can also be implemented in hardware blocks separate from the control/timing circuit. For example, separate blocks of hardware may be used to implement portions of the flow charts separate from the control/timing circuit, e.g., a threshold setting circuit (e.g., blocks 318–326, 340–346, 366–372), condition detection circuit (e.g., block 302), success detector circuit (e.g., blocks 314, 336, 362). Such implementations are considered to be within the scope of the present invention. It is therefore to be understood that within the scope of the claims, the invention may be practiced otherwise than as specifically described herein.

What is claimed is:

1. An implantable cardiac stimulation device for providing therapy to a patient's heart, the device comprising:
    a sense amplifier that senses signals from the patient's heart and generates signals related to the patient's heart rate;
    a memory circuit for storing threshold settings for determining the type of antiarrhythmic therapy to be applied to the patient's heart for a range of heart rates defined by the stored threshold settings;
    a control and timing circuit coupled to the sense amplifier and the memory circuit that generates control signals responsive to the sense signals and the threshold settings, the control signals defining one of a plurality of antiarrhythmic therapies, wherein the therapy is selected in accordance with the relationship of the sensed heart rate and the stored threshold settings;
    a pulse generator that generates therapeutic pulses to the patient's heart in response to the control signals; and
    a rate threshold adjusting circuit being adapted to adjust the threshold settings stored in the memory circuit in accordance with the response of the patient to the selected antiarrhythmic therapy.

2. The device of claim 1 wherein the patient's heart beats at a ventricular rate and the threshold settings are related to the ventricular rate of the patient's heart.

3. The device of claim 1 wherein the threshold settings define a ventricular tachycardia zone and a ventricular fibrillation zone, and wherein the pulse generator generates antitachycardia pacing therapy pulses when the sensed heart rate corresponds to the ventricular tachycardia zone and defibrillation shocks when the sensed heart rate corresponds to the ventricular fibrillation zone.

4. The device of claim 1 wherein the control and timing circuit determines a cardiac condition of the patient based on the ventricular rate and the stored threshold settings.

5. The device of claim 1 wherein the threshold settings define ventricular rate ranges, each range corresponding to a cardiac condition, and wherein the control and timing circuit determines the cardiac condition based on a ventricular rate corresponding to one of the ranges.

6. The device of claim 5 wherein the control and timing circuit further determines the cardiac condition based on a secondary criteria.

7. The device of claim 6 wherein the secondary criteria comprises sudden onset, wherein the control and timing circuit determines that physiological sinus rhythm is present when the sudden onset criteria is not met, and determines that a pathological rhythm is present when the sudden onset criteria is met.

8. The device of claim 6 wherein the secondary criteria comprises an indication that the patient is exercising.

9. The device of claim 6 wherein the secondary criteria comprises a mean ventricular rate interval ($VRI_M$) within a respective zone.

10. The device of claim 6 wherein the secondary criteria comprises a success rate of converting the patient's rhythm to a normal rhythm.

11. The device of claim 6 wherein the control and timing circuit adjusts the threshold in the direction of the mean ventricular rate interval ($VRI_M$) within a respective zone.

12. The device of claim 10 wherein the control and timing circuit determines that a threshold adjustment is needed when the success rate is low, and determines that a threshold adjustment is not needed when the success rate is high.

13. The device of claim 1 wherein the memory circuit additionally stores a plurality of rules, wherein the threshold adjusting circuit adjusts the threshold setting using the stored rules.

14. The device of claim 1 wherein the threshold settings define a slow ventricular tachycardia zone and a fast ventricular tachycardia zone, and wherein the pulse generator generates less aggressive antitachycardia therapy when the sensed heart rate corresponds to the slow ventricular tachycardia zone, and generates more aggressive antitachycardia therapy when the sensed heart rate corresponds to the fast ventricular tachycardia zone.

15. The device of claim 1 wherein the threshold settings define a normal sinus rhythm zone and a ventricular tachycardia zone, and the pulse generator generates no therapy when the sensed heart rate corresponds to the normal sinus rhythm zone, and generates antitachycardia therapy when the sensed heart rate corresponds to the ventricular tachycardia zone.

16. An implantable cardioversion device generating antitachyarrhythmic therapy for a patient's heart, the device comprising:
   a sense amplifier receiving intrinsic signals indicative of ventricular activity and generating corresponding sense signals;
   a condition detector receiving the sense signals and generating patient condition signals indicative of the condition of the patient based on the sense signals and a set of thresholds;
   a threshold level setting circuit that generates the thresholds;
   a timing and control circuit that generates command signals based on the patient condition signals and the sense signals, the command signals defining a therapy for the patient corresponding to the patient condition signals;
   an output signal generator receiving the commands and responsively generating therapeutic pulses to revert the patient condition to a sinus state;
   a therapy success detector that analyzes the therapeutic pulses to determine a success rate at which said therapeutic pulses have reverted the patient condition to a sinus state; and wherein
   the threshold setting circuit is coupled to the therapy success detector to adjust the threshold levels in accordance with the determined success rate.

17. The device of claim 16 wherein the condition detector detects the condition based on the ventricular rate.

18. The device of claim 17 wherein the condition detector further detects the patient's condition based on a secondary criteria.

19. The device of claim 18 wherein the secondary criteria comprises sudden onset, wherein the control and timing circuit determines that physiological sinus rhythm is present when the sudden onset criteria is not met, and determines that a pathological rhythm is present when the sudden onset criteria is met.

20. The device of claim 18 wherein the secondary criteria comprises an indication that the patient is exercising.

21. The device of claim 18 wherein the secondary criteria comprises a mean ventricular rate interval ($VRI_M$) within a respective zone.

22. The device of claim 21, wherein the control and timing circuit adjusts the threshold in the direction of the mean ventricular rate interval ($VRI_M$) within a respective zone.

23. The device of claim 16 wherein the condition detector compares the ventricular rate to a plurality of sets of ranges to determine if the ventricular rate is within one of the sets of ranges, the ranges defining various tachyarrhythmia conditions for the patient's heart.

24. The device of claim 16 wherein the condition detector compares the ventricular rate to a plurality of sets of ranges defining a sinus rhythm, a ventricular tachyarrhythmia and a ventricular fibrillation/flutter condition.

25. The device of claim 24 wherein the sets of ranges correspond to the levels set by the threshold setting circuit.

26. The device of claim 16 further comprising a memory storing a plurality of rules for determining the conditions under which the thresholds are changed, and wherein the threshold setting circuit is coupled to the memory to apply the rules to the current thresholds in accordance with the cardiac condition of the patient as determined by the condition detector and the success rate.

27. The device of claim 16 wherein the control and timing circuit determines that a threshold adjustment is needed when the success rate is low, and determines that a threshold adjustment is not needed when the success rate is high.

28. In an implantable cardioversion device which includes a sensor for sensing cardiac activity in a patient's heart, a patient condition detector that identifies the patient's cardiac condition based on the cardiac activity and a set of thresholds, and a pulse generator configured for generating antitachyarrhythmic signals in accordance with the output of the patient condition detector, a process of dynamically adjusting the set of thresholds comprising the steps of:
   setting the set of thresholds to predetermined values;
   operating the device using the predetermined values; and
   adjusting the thresholds dynamically by changing the predetermined threshold values in accordance with the cardiac activity resulting in response to the antitachyarrhythmic signals.

29. The method of claim 28 wherein the thresholds define a sinus rhythm condition, a tachycardia condition and a fibrillation/flutter condition.

30. The method of claim 28 wherein the device includes a memory storing rules defining how the threshold values are changed and further comprising applying the rules for adjusting the threshold values.

31. The method of claim 28 further comprising determining a success rate indicative of whether a therapy dependent on the antitachyarrhythmic signals has successfully reverted the patient's heart to a normal sinus rhythm.

32. The method of claim 31 wherein the step of adjusting the thresholds is dependent on the success rate.

33. The method of claim 28 wherein the sensed cardiac activity corresponds to the ventricular rate.

34. The method of claim 28 wherein the antitachyarrhythmic signals are selected from the set of cardioversion pacing pulses and defibrillation shocks.

35. The method of claim 28 wherein the step of adjusting the thresholds is dependent on sudden onset of the cardiac activity.

36. The method of claim 28 wherein the step of adjusting the thresholds is dependent on whether there is an indication that the patient is exercising.

37. The method of claim 28 wherein the step of adjusting the thresholds is dependent on a mean ventricular rate interval.

38. The method of claim 37 wherein the adjusting step comprises the step of adjusting the threshold in the direction of the mean ventricular rate interval ($VRI_M$) within a respective zone.

39. The method of claim 28 wherein the adjusting step comprises the step of adjusting the threshold when the success rate is low.

* * * * *